United States Patent [19]

Shah

[11] 4,325,939

[45] Apr. 20, 1982

[54] ZINC DERIVATIVES AND THEIR USE IN DENTAL COMPOSITIONS

[75] Inventor: Nutan B. Shah, New Rochelle, N.Y.

[73] Assignee: Richardson-Vicks Inc., Wilton, Conn.

[21] Appl. No.: 189,152

[22] Filed: Sep. 22, 1980

[51] Int. Cl.³ .................. A61K 7/16; A61K 7/24; A61K 31/315; C07F 3/06

[52] U.S. Cl. .................... 424/55; 424/49; 424/289; 260/429.9

[58] Field of Search .............. 260/429.9; 424/55, 54, 424/52, 49, 48, 50, 289

[56] References Cited

U.S. PATENT DOCUMENTS

| | | | |
|---|---|---|---|
| 3,824,279 | 7/1974 | Lamberti | 260/429.9 |
| 3,887,704 | 6/1975 | Lichtenstein | 424/289 |
| 4,082,841 | 4/1978 | Pader | 424/50 |
| 4,100,269 | 7/1978 | Pader | 424/55 |
| 4,138,477 | 2/1979 | Gaffar | 424/52 |
| 4,144,323 | 3/1979 | Lamberti | 424/49 |
| 4,160,820 | 7/1979 | Wagenknecht | 424/48 |
| 4,160,821 | 7/1979 | Sipos | 424/55 |
| 4,196,189 | 4/1980 | Raaf et al. | 424/52 |

OTHER PUBLICATIONS

Chemical Abstract, vol. 77, #143745x, 8/17/72, Hoyles, "Dentifrice".

Chemical Abstract, vol. 74, #55510z, 12/23/70, Barth, "Cleansing Compositions for Dentures".

Primary Examiner—Thomas A. Waltz
Assistant Examiner—Raymond Covington
Attorney, Agent, or Firm—George W. Rauchfuss, Jr.

[57] ABSTRACT

A novel zinc compound, an alkali metal or ammonium zinc citrate, is prepared for use in dental compositions and especially in mouthwash compositions to provide mouthwashes with less astringency without loss of antiodor properties, improved water solubility of the zinc compound and improved chemical compatibility when ionic fluoride salts are employed in compositions along with the zinc compound.

8 Claims, No Drawings

ZINC DERIVATIVES AND THEIR USE IN DENTAL COMPOSITIONS

FIELD OF THE INVENTION

This invention relates to a novel zinc compound and the use thereof in dental compositions and especially in mouthwash compositions.

BACKGROUND OF THE INVENTION

The beneficial effect of zinc compounds in dental compositions, especially in toothpastes and mouthwashes, has been generally recognized for some time. In U.S. Pat. No. 4,100,269, issued July 11, 1978 to Morton Pader, there is disclosed the use of insoluble zinc compounds in dentifrices for improving the control of calculus. Insoluble zinc compounds employed in the patent are those having a solubility of less than about one gram of zinc per 100 cc of water at 20° C. and preferably a solubility of not more than about 0.5 gram zinc compound per 100 cc water at 20° C. Among the typical insoluble zinc compounds employed in the patent is zinc citrate. Zinc acetate and hydroxide have been recognized as having anti-plaque properties in dentifrices as disclosed in Hanke, M. T., J. Amer. Dental Assoc., 27(9), 1379–93 (1940). The pyrophosphate, tetrametaphosphate, metaphosphate and orthophosphate salts of zinc have been known to be effective in tartar removal as disclosed in W. German Patent Specification No. 1,251,468, assigned to Chemische Fabrik Budenheim and published Oct. 5, 1967. Also it has been known to formulate tooth powders containing zinc citrate and calcium gluconate such as disclosed in U.S. Pat. No. 1,861,189 issued May 31, 1932 to Charles Pfizer.

In addition, zinc chloride has been used in mouthwash compositions and recognized as possessing anti-mouth odor properties in said compositions.

However, despite the heretofore known use of zinc compounds in dental compositions their use has not been without certain undesirable drawbacks and side-effects. For example, when such zinc compounds have been employed it has not been possible to satisfactorily include ionic fluoride in the compositions due to the chemical incompatibility therebetween. Moreover, while zinc chloride possesses the desired anti-odor activity, its high level of astringency is undesirable. Yet other zinc compounds, such as for example, zinc citrate are so slightly soluble in aqueous solutions that while the level of astringency is kept acceptably low, there is an undesirable loss in anti-mouth odor activity of the zinc compound.

It is therefore highly desirable to provide a zinc derivative that is less astringent than zinc chloride so as to provide enhanced acceptance by users of dental compositions containing same yet without sacrificing anti-odor activity. It is also desirable to provide a zinc derivative having higher aqueous solubility than zinc citrate yet not as astringent as zinc chloride. Additionally it is desirable to provide a zinc derivative of said properties that does not present substantially any chemical incompatibility problem in dental compositions employing an ionic fluoride salt.

BRIEF DESCRIPTION OF THE INVENTION

In accordance with the invention a novel zinc derivative, an alkali metal or ammonium zinc citrate, and preferably, sodium zinc citrate, possessing such desired properties is provided and permits the formulation of dental compositions of improved properties.

DETAILED DESCRIPTION OF THE INVENTION

An alkali metal or ammonium zinc citrate, $C_6H_5O_7MZn$, wherein M is ammonium or an alkali metal, preferably sodium or potassium, is prepared by the reaction of equimolar amounts of ammonium hydroxide or an alkali metal hydroxide, such as sodium hydroxide, with zinc oxide and citric acid.

The reaction can be carried out, for example, at room temperature in water as per the following Example.

EXAMPLE

In a reaction vessel 21.04 g citric acid, hydrous, is dissolved in 100 g water. To this solution 8.14 g zinc oxide is added in small quantities and the reaction mixture stirred. After the reaction of the zinc oxide with the citric acid 4.0 g sodium hydroxide is added and the reaction mixture stirred until all the sodium hydroxide is reacted. At the end of the reaction, a clear solution is obtained. The solution is treated with absolute ethyl alcohol to precipitate out the sodium zinc citrate salt. The salt crystals are filtered off and dried overnight in a 45° C. oven. Elemental Analysis. Calculated: Zn, 20.8; C, 22.90; H, 2.88; Na, 7.30. Found: Zn, 22.1; C, 22.84; H, 3.13; Na, 5.70. The pH of a 2.5% suspension of the salt is 6.32 and the solubility of the salt in water at 25° C. is 1.17 g/100 ml.

In a similar manner other alkali metal zinc citrate salts can be prepared by the use of other alkali metal hydroxides or ammonium hydroxide in place of sodium hydroxide in the Example, such as for example, potassium zinc citrate is prepared when potassium hydroxide is employed.

The ammonium or alkali metal zinc citrate compounds of this invention are useful in dentifrice compositions, especially in mouthwash compositions. The new compounds, especially sodium zinc citrate is considerably less astringent than zinc chloride which is now used in mouthwash compositions and, therefore, is of greatly enhanced acceptability yet without sacrificing its anti-odor property. Furthermore, the compounds of this invention possess high aqueous solubility and permits one to formulate concentrated mouthwash formulations. Additionally, the compounds of this invention can be added to dentifrice compositions, such as mouthwashes, containing an ionic fluoride salt and without any significant chemical instability.

In dentifrice compositions the compounds of this invention are employed in amounts of from about 0.1 to about 15.0%, preferably about 0.2 to about 5%, and most preferably about 0.5 to about 2.0%, by weight based on the total weight of the composition so as to provide from about 7 to about 28 mg/kg body weight of the user thereof. The dentifrice compositions of the present invention comprise the aforesaid ammonium or alkali metal zinc citrate salts and a carrier suitable for use in the oral cavity. The carrier can be water or an organic solvent such as alcohol. Preferably, however, the carrier portion of the oral composition is a conventional toothpaste, mouthwash, chewing gum or the like.

Dentifrices usually contain surface-active agents also called sudsing agents. Suitable surface-active agents are those which are reasonably stable and form suds throughout a wide pH range, that is, nonsoap nonionic, cationic, and amphoteric organic synthetic detergents.

The nonionic synthetic detergents which can be used with the oral compositions of the present invention may be broadly defined as compounds produced by the condensation of a hydrophilic alkylene oxide group with an organic hydrophobic compound which may be aliphatic or alkyl-aromatic in nature. The length of the hydrophyllic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol.

Other suitable nonionic synthetic detergents include: the polyethylene oxide condensates of alkyl phenols, those derived from the condensation of ethylene oxide with the product resulting from the reaction of propylene oxide and ethylene diamine, the condensation product of aliphatic alcohols having from 8 to 18 carbon atoms, in either straight chain or branched chain configuration, with ethylene oxide, and the polyoxyethylene derivatives of fatty acid partial esters of sorbitol anhydride and available in the market under the trade name "Tween."

Cationic synthetic detergents useful in the oral compositions of the present invention can be broadly defined as quaternary ammonium compounds having one long alkyl chain containing from about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconutalkyltrimethylammonium nitrite, cetyl pyridinium fluoride, and the like.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, for example, carboxylate, sulfonate, sulfate, phosphate, or phosphonate.

Many additional nonionic, cationic and amphoteric synthetic detergents are known to the art and can be used as sudsing agents in the compositions herein. Further examples can be found in *McCutcheon's Detergents and Emulsifiers.*

The sudsing agent can be employed at levels ranging from about 0.5% to about 5.0% of the dentifrice composition.

Dentifrices normally also contain flavoring agents. Suitable flavoring agents for use in the dentifrices herein include, for example, wintergreen oil (methyl salicylate), oil of peppermint, oil of sassafras (synthetic), and oil of anise. Flavoring agents are present at a level of from 0.01% to 2.0%.

Dentifrices normally also contain sweetening agents. Suitable sweetening agents for use in dentifrices include for example saccharin, dextrose and levulose. The sweetening agents are used at levels of from about 0.05% to about 2%.

In toothpastes it is desirable to employ thickening agents such as hydroxyethylcellulose and water-soluble salts of cellulose ethers, including sodium carboxymethyl cellulose and sodium carboxymethylhydroxyethyl cellulose; or natural gums, including gum karaya, gum arabic, and gum tragacanth. Also, colloidal magnesium aluminum silicate or finely divided silica can be used as part of the thickening agent to improve the texture of the product. Thickening agents are used at levels of from 0.1% to 5.0% of the toothpaste composition.

It is also desirable to include a humectant material in toothpastes. Suitable materials for this purpose include glycerine, sorbitol, and other edible polyhydric alcohols or mixtures thereof. These materials can comprise from about 1% to about 50% of the toothpaste composition. In addition to the aforementioned typical components of a toothpaste, water usually comprises the balance of the toothpaste, and is usually present at levels up to about 50%.

Mouthwashes generally comprise a water/ethyl alcohol solution and optionally other ingredients such as flavor, sweeteners, and humectants such as those mentioned above for dentifrices. The alcohol provides an antibacterial effect. Optionally, mouthwashes also contain sudsing agents. Humectants such as glycerine and sorbitol give a moist feel in the mouth and are desirably also present. Antibacterial agents are sometimes incorporated into mouthwashes or dentifrices at levels from about 0.01% to about 2.0%.

Generally, mouthwashes suitable for use as carriers herein contain: 5% to 40% ethyl alcohol; 0% to 20%, preferably 5% to 20%, glycerine or other humectant; 0% to 12%, preferably 0.1% to 12%, sudsing agent, 0% to 0.5%, preferably 0.05% to 0.5%, sweetening agent such as saccharin; and 0% to 0.3%, preferably 0.05% to 0.3%, flavoring agent; and the balance, water with colorants or dyes if desired.

Chewing gum suitable for use as a carrier herein comprises a gum base and flavoring materials such as those mentioned above for dentifrices. The flavoring materials are present at a level of 0.01% to about 2.0% of the final chewing gum composition. The gum base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Optionally, corn syrup is added as a softener and binder for the chewing gum and sugar is optionally added as a filler and sweetener. A typical chewing gum suitable as a carrier herein comprises 15% to 30% gum base, 15% to 20% corn syrup, 50% to 65% sugar, and 0.05% to 1.5% flavoring materials.

Lozenges suitable as carriers herein comprise a hard sugar candy base and one or more flavoring materials. The flavoring materials are present at levels between 0.01% to 2.0%. Optionally, lozenges can contain various other materials. A typical lozenge suitable as a carrier in this invention is a hard candy comprised of a hard candy base containing 0.05% to 1.5% flavor. The hard candy base is a solidified solution of amorphous sugar which is generally formed from a sugar solution which has been cooked at high temperature so as to remove nearly all of the moisture. The flavoring materials are added before the moisture is removed. The flavoring materials mentioned hereinbefore for dentifrices are also exemplary of those suitable for use in lozenges.

The oral compositions of the present invention can also optionally contain additional therapeutic materials for use in the oral cavity such as anticaries agents, for example, water-soluble fluoride such as sodium fluoride and stannous fluoride.

This invention is further illustrated by the following formulations.

FORMULATION A

A toothpaste is prepared according to the following formula:

| Component | Parts by Weight |
| --- | --- |
| Sorbitol (70% soln.) | 20.00 |
| Sodium saccharin | 0.21 |
| Veegum (colloidal magnesium aluminum silicate) | 0.40 |
| Calcium carbonate (abrasive) | 30.00 |
| Flavor | 1.00 |
| Sodium carboxymethylcellulose | 1.30 |
| Glycerine | 10.00 |
| Sodium zinc citrate | 0.70 |
| Polyoxyethylene sorbitan (20) monoisostearate | 1.50 |
| Distilled water | balance to 100.00 |

FORMULATION B

A mouthwash in accordance with the present invention is formulated as follows:

| Component | Parts by Weight |
| --- | --- |
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Flavoring | 0.16 |
| Sodium zinc citrate | 0.20 |
| Color | 0.50 |
| Sorbitol (70% in water) | 12.00 |
| Distilled water | balance to 100.00 |

FORMULATION C

A chewing gum in accordance with the present invention is formulated as follows:

| Component | Parts by Weight |
| --- | --- |
| Gum base | 21.30 |
| Ester Gum | 6.40 |
| Coumarone resin | 9.60 |
| Dry latex rubber | 3.20 |
| Paraffin wax (M.P.180° F.) | 2.10 |
| Surgar | 58.45 |
| Corn syrup (Baume 45) | 18.20 |
| Flavoring | 1.05 |
| Sodium zinc citrate | 1.00 |

FORMULATION D

Another toothpaste is prepared according to the following formula:

| Component | Parts by Weight |
| --- | --- |
| Glycerin | 10.00 |
| Sorbitol (70% in water) | 10.00 |
| Insoluble metaphosphate | 30.00 |
| Sodium lauryl sulfate | 1.50 |
| Flavor | 1.00 |
| Sodium carboxymethylcellulose | 1.00 |
| Magnesium aluminum silicate (Veegum, regular) | 0.80 |
| Methylparaben | 0.06 |
| Propylparaben | 0.02 |
| Sodium zinc citrate | 1.78 |
| Sodium saccharin | 0.20 |
| Colloidal silica (Cab-O-Sil) | 1.50 |
| Distilled water | balance to 100.00 |

FORMULATION E

A four-fold mouthwash concentrate is prepared according to the following formula:

| Component | Parts by Weight |
| --- | --- |
| Alcohol (95% in water) | 21.14 v/v |
| Glycerin | 9.99 |
| Pluronic F-127 | 4.00 |
| Flavor | 0.53 |
| Saccharin, insoluble | 0.20 |
| Menthol | 0.15 |
| Cetylpipidinium chloride | 0.10 |
| Colorants | 0.06 |
| Sodium zinc citrate | 1.78 |
| Distilled water | balance to 100.00 |

What is claimed is:

1. A compound selected from the group consisting of an ammonium or an alkali metal zinc citrate.

2. An alkali metal zinc citrate of claim 1 which is sodium zinc citrate.

3. A dentifrice composition comprising about 0.1 to about 15.0% by weight of an ammonium or alkali metal zinc citrate in a carrier suitable for use in an oral cavity.

4. A dentifrice composition of claim 3 wherein the citrate compound is present in an amount of from about 0.2 to about 5.0% by weight.

5. A dentifrice composition of claim 3 wherein the citrate compound is present in an amount of from about 0.5 to about 2.0% by weight.

6. A dentifrice composition of claim 4 wherein the alkali metal zinc citrate is sodium zinc citrate.

7. A dentifrice composition of claim 5 which is a mouthwash comprising about 5 to about 40% by weight ethyl alcohol, about 0 to 20% by weight humectant, about 0 to 12% by weight surface active agent, about 0 to 0.5% by weight sweetening agent, about 0 to 0.3% by weight flavoring agent, and the balance water.

8. A mouthwash composition of claim 7 wherein the alkali metal zinc citrate is sodium zinc citrate.

* * * * *